(12) United States Patent
Diamond et al.

(10) Patent No.: US 7,931,619 B2
(45) Date of Patent: Apr. 26, 2011

(54) POWER INJECTION CATHETERS

(75) Inventors: Jordan P. Diamond, Salt Lake City, UT (US); Abtihal Raji-Kubba, Salt Lake City, UT (US); William R. Barron, Riverton, UT (US); Catherine C. Breiter, Holladay, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 1052 days.

(21) Appl. No.: 11/029,299

(22) Filed: Jan. 4, 2005

(65) Prior Publication Data

US 2006/0149189 A1    Jul. 6, 2006

(51) Int. Cl.
A61M 1/00    (2006.01)
(52) U.S. Cl. .................................................. 604/118
(58) Field of Classification Search .............. 604/118, 604/246, 523
See application file for complete search history.

(56) References Cited

U.S. PATENT DOCUMENTS

| | | | |
|---|---|---|---|
| 3,543,759 A | 12/1970 | McWhorter | |
| 3,677,243 A | 7/1972 | Nerz | |
| 3,921,631 A | 11/1975 | Thompson | |
| 4,000,741 A * | 1/1977 | Binard et al. | 604/121 |
| 4,044,793 A | 8/1977 | Krueger et al. | |
| 4,123,091 A | 10/1978 | Cosentino et al. | |
| 4,240,430 A | 12/1980 | Binard et al. | |
| 4,403,988 A | 9/1983 | Binard et al. | |
| 4,439,182 A * | 3/1984 | Huang | 604/85 |
| 4,451,256 A | 5/1984 | Weikl et al. | |
| 4,471,778 A | 9/1984 | Toye | |
| 4,502,502 A * | 3/1985 | Krug | 137/512.3 |
| 4,563,180 A | 1/1986 | Jervis et al. | |
| 4,671,786 A | 6/1987 | Krug | |
| 4,722,725 A * | 2/1988 | Sawyer et al. | 604/27 |
| 4,787,886 A | 11/1988 | Cosman | |
| 4,795,431 A * | 1/1989 | Walling | 604/97.02 |
| 4,883,459 A * | 11/1989 | Calderon | 604/28 |
| 4,967,703 A | 11/1990 | Donnez | |
| 4,976,703 A * | 12/1990 | Franetzki et al. | 604/247 |
| 5,169,393 A * | 12/1992 | Moorehead et al. | 604/247 |
| 5,201,722 A * | 4/1993 | Moorehead et al. | 604/247 |
| 5,205,834 A * | 4/1993 | Moorehead et al. | 604/247 |
| 5,292,305 A | 3/1994 | Boudewijn et al. | |
| 5,318,588 A | 6/1994 | Horzewski et al. | |
| 5,380,276 A | 1/1995 | Miller et al. | |
| 5,380,301 A | 1/1995 | Prichard et al. | |
| 5,556,386 A * | 9/1996 | Todd | 604/247 |
| 5,569,197 A | 10/1996 | Helmus et al. | |

(Continued)

OTHER PUBLICATIONS

Brown et al., "Power Injection of Microcatheters: An In Vitro Comparison", J Vasc Interv Radiol 2005; 16:101-106.

(Continued)

*Primary Examiner* — Nicholas D Lucchesi
*Assistant Examiner* — Aarti B Berdichevsky
(74) *Attorney, Agent, or Firm* — Rutan & Tucker, LLP

(57) ABSTRACT

A power injection catheter for high flow rate delivery of fluids. The power injection catheter may include a pressure relief mechanism for preventing overpressurizing within the lumen of the catheter. The pressure relief mechanism may be configured to prevent sudden pressure build-up inside the catheter lumen by absorbing, buffering or releasing pressure inside the lumen during pressure spikes. The power injection catheter may also take the form of a multi-lumen catheter capable of simultaneous infusions of a single fluid through two or more of the lumens in the catheter.

15 Claims, 7 Drawing Sheets

U.S. PATENT DOCUMENTS

| | | | |
|---|---|---|---|
| 5,707,356 A * | 1/1998 | Paul | 604/119 |
| 5,713,849 A * | 2/1998 | Bosma et al. | 604/28 |
| 5,752,522 A * | 5/1998 | Murphy | 600/587 |
| 5,830,196 A | 11/1998 | Hicks | |
| 5,843,044 A * | 12/1998 | Moorehead | 604/247 |
| 5,902,282 A | 5/1999 | Balbierz | |
| 5,984,902 A * | 11/1999 | Moorehead | 604/247 |
| 5,989,206 A | 11/1999 | Prosl et al. | |
| 6,033,393 A | 3/2000 | Balbierz et al. | |
| 6,190,354 B1 * | 2/2001 | Sell et al. | 604/96.01 |
| 6,290,265 B1 * | 9/2001 | Warburton-Pitt et al. | 285/131.1 |
| 6,520,977 B2 | 2/2003 | Piraka | |
| 6,575,959 B1 | 6/2003 | Sarge et al. | |
| 6,592,544 B1 * | 7/2003 | Mooney et al. | 604/43 |
| 6,595,966 B2 | 7/2003 | Davey et al. | |
| 6,620,118 B1 | 9/2003 | Prosl et al. | |
| 6,638,242 B2 | 10/2003 | Wilson et al. | |
| 6,689,096 B1 * | 2/2004 | Loubens et al. | 604/96.01 |
| 6,966,893 B2 * | 11/2005 | Holtby et al. | 604/146 |
| 7,025,716 B1 * | 4/2006 | Meloul et al. | 600/7 |
| 7,252,652 B2 * | 8/2007 | Moorehead et al. | 604/247 |
| 2002/0062119 A1 * | 5/2002 | Zadno-Azizi | 604/509 |
| 2004/0054348 A1 | 3/2004 | Hogendijk | 604/523 |
| 2006/0089604 A1 * | 4/2006 | Guerrero | 604/247 |
| 2006/0149189 A1 * | 7/2006 | Diamond et al. | 604/118 |
| 2007/0093764 A1 * | 4/2007 | Guerrero | 604/284 |
| 2007/0129692 A1 * | 6/2007 | Enomoto et al. | 604/284 |
| 2007/0161940 A1 * | 7/2007 | Blanchard et al. | 604/6.1 |
| 2007/0173777 A1 * | 7/2007 | Murphy | 604/247 |
| 2007/0173786 A1 * | 7/2007 | Recinella et al. | 604/523 |

OTHER PUBLICATIONS

Coyle, et al., "Power Injection of Contrast Media via Peripherally Inserted Certral Catheters for CT", J Vasc Interv Radiol 2004; 15:809-814.

Federle et al., "Frequency and Effects of Extravasation of Ionic and Nonionic CT Contrast Media During Rapid Bolus Injection", Radiology 1998; 206:637-640.

Herts et al., "Power Injection of Intravenous Contrast Material through Central Venous Catheters for CT: In Vitro Evaluation", Radiology 1996; 200:731-735.

Jacobs et al., "Contrast Media Reactions and Extravasation: Relationship to Intravenous Injection Rates", Radiology 1998; 209:411-416.

Lowery et al., "Modified Umbilical Artery Catheter for Power-Injection Aortography", Radiology 105:711-712, Dec. 1972.

Miles et al., "Safe Use of an Intravenous Power Injector for CT: Experience and Protocol", Radiology 1990; 176:69-70.

Rivitz et al., "Power Injection of Peripherally Inserted Central Catheters", JVIR 1997; 8:857-863.

Ruess et al., "In-line Pressures Generated in Small-Bore Central Venous Catheters During Power Injection of CT Contrast Media", Radiology 1997; 203:625-629.

Salis et al., "Maximal Flow Rates Possible During Power Injection Through Currently Available PICCs: An In Vitro Study", J Vasc Interv Radiol 2004; 15:275-281.

Sanelli et al., "Safety and Feasibility of Using a Central Venous Catheter for Rapid Contrast Injection Rates", AJR 2004; 183:1829-1834.

Walsh et al., "Effect of Contrast Agent Viscosity and Injection Flow Velocity on Bolus Injection Pressures for Peripheral Venous Injection in First-Pass Myocardial Perfusion Studies", Technology and Health Care 10 (2002) 57-63.

Williamson et al., "Assessing the Adequacy of Peripherally Inserted Central Catheters for Power Injection of Intravenous Contrast Agents for CT", J Comput Assist Tomogr, 25(6); 932-937.

* cited by examiner

POWER INJECTION CATHETERS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A COMPACT DISK APPENDIX

Not applicable.

BACKGROUND OF THE INVENTION

It has been observed that during injection of a contrast media at high flow rates into a small-sized lumen, the sudden increase in pressure inside the lumen may lead to failure of the catheter wall. In addition, catheters that are implanted in a patient's body for a period of time may have thrombus build-up within the lumen of the catheter. These thromboses may occlude the catheter and cause overpressurization when the catheter is flushed. To prevent the sudden pressure spikes, a pressure buffering component may be provided to modulate the pressure inside the catheter lumen. Various other medical applications that require high throughput fluid injection through a catheter may also benefit from having a pressure modulating device integrated within the catheter to prevent overpressurizing and/or to provide an indicator to the operator that the catheter is being overloaded.

Examples of various overpressure protection devices are disclosed in U.S. Pat. No. 3,543,759, titled "CATHETER WITH SAFETY INDICATOR" issued to McWhorter, dated Dec. 1, 1970; U.S. Pat. No. 4,000,741, titled "SYRINGE ASSEMBLY" issued to Binard et al., dated Jan. 4, 1977; U.S. Pat. No. 4,240,430, titled "SYRINGE ASSEMBLY" issued to Binard et al., dated Dec. 23, 1980; U.S. Pat. No. 4,403,988, titled "SYRINGE ASSEMBLY" issued to Binard et al., dated Sep. 13, 1983; U.S. Pat. No. 4,671,786, titled "OVERPRESSURE SAFETY VALVE" issued to Krug, dated Jun. 9, 1987; U.S. Pat. No. 6,033,393, titled "METHOD AND APPARATUS FOR OVERPRESSURE PROTECTION OF A CATHETER" issued to Balbierz et al., dated Mar. 7, 2000; U.S. Pat. No. 6,520,977 B2, titled "UTERINE BALLOON APPARATUS AND METHOD" issued to Piraka, dated Feb. 18, 2003; each of which is incorporated herein by reference in its entirety.

Many of the devices disclosed above are design for low flow applications. Furthermore, in a pressure protection device that is based on a compliant balloon, the balloon will typically enlarge gradually in response to pressure, and therefore does not provide a clear indication to the operator when a critical pressure threshold has been breached. Thus, in applications where high pressure injections are required, the operators may have difficulty determining whether overpressurization has occurred by observing the condition of a partially inflated balloon alone. In addition, many of these designs may fail at high pressure, such as 300 psi or above. The compliant nature of the pressure protection mechanisms in these devices may also prevent high pressure from being maintained within the catheter, since many of the compliant balloons will start to expand at a relatively low pressure. These designs tend to have a low pressure threshold, and, as a result, the overall fluid throughput is also relatively low. In addition, many of the disclosed devices have flow paths with high flow resistance.

For power injection applications where a high fluid infusion rate is necessary, it may be desirable to have a pressure buffering device that allows one to maintain high pressure, such as 300 psi or above, within the lumen of the catheter, but at the same time is capable of modulating sudden pressure peaks. Sudden pressure spikes due to initial introduction of fluid pressure, unanticipated obstruction within the catheter, or operator error, may temporarily force the pressure inside the catheter to exceed the breaking threshold (i.e., burst value) of the catheter. However, for high flow rate injection a relatively high pressure needs to be maintained within the catheter to maintain the high throughput. Thus, a device that can prevent pressure spikes and overpressurization, but at the same time allows the system to maintain a relatively high pressure within the catheter to support high flow rate application may be desirable.

In addition, it may be desirable to have a catheter that can be configured with a low resistance flow path to maximize flow rate for power injection applications. A catheter that can be configured to minimize flow resistance and support high fluid flow rate may be particularly useful for power injection applications.

BRIEF SUMMARY OF THE INVENTION

Described herein are catheters for infusing fluids into a patient's body. Some variations of the catheter are configured for high flow rate applications. These catheters, which are configured for infusing large amounts of fluids in a short period of time, are termed "power injection catheters." The catheters may be configured to support high pressure inside its lumen to sustain high pressure generated by rapid infusion. In addition, a pressure relief mechanism may be provided on the catheter to prevent overpressurization. In one variation, the power injection catheter comprises a pressure buffering component/unit connected to or integrated into the proximal portion of a catheter. The pressure buffering component prevents sudden pressure build-up inside the lumen of the catheter by (1) absorbing/buffering, or (2) releasing pressure inside the lumen during pressure spikes. The buffering component may comprise a balloon, a diaphragm, or a pressure relief valve, etc. In one configuration, the balloon or diaphragm comprises a non-compliant polymeric material. In another configuration, the balloon or diaphragm comprises a compliant polymeric material.

In another variation, a T-shaped connector is provided for connection to the proximal end of a catheter. The distal end of the T-shape connector is connected to the proximal end of the catheter, and the proximal end of the T-shaped connector can be connected to a fluid source. The perpendicular opening at the mid-section of the T-shaped connector may be covered with a diaphragm, a balloon, a burst disk, or a pressure relief valve. The T-shaped connector may also be designed with a replaceable pressure relief mechanism, such that if overpressurizing causes the pressure relief mechanism to fail, it can be easily replaced. In one configuration, the T-shaped connecter is implemented with a pressure relief mechanism and a balloon positioned over the pressure relief mechanism. The pressure relief mechanism opens when the pressure within the connector exceeded a predefined threshold. The balloon serves as a mechanism to capture the effluent.

In another variation, a burst disk is implemented along the fluid infusion path to prevent catheter infusion pressure from breaching a predefined critical pressure threshold. The burst disk may be configured to break and release the pressure within the lumen of the catheter at a pressure threshold that is below the burst value of the catheter body. In one particular design, the burst disk is implemented with a fluid containment balloon to provide a definite indicator of overpressurizing. In this design, when the catheter lumen pressure is below the pre-defined pressure threshold supported by the burst disk, the balloon positioned over the burst disk remains collapsed. When the lumen pressure exceeds the predefined pressure threshold supported by the burst disk, the burst disk is compromised and breaks. As a result, the balloon inflates and provides an immediate indicator to the operator that the device has been overpressurized. The balloon also contains the fluids that are exiting the catheter lumen through the compromised burst disk.

Another method to address the high pressure problem associated with power injection is to increase the available cross-sectional area for the fluid flow to minimize pressure increase within the catheter. Power injection through small diameter lumen will result in generation of high pressure (e.g., about 300 psi) because the small cross-sectional area has to support the high flow rate. One way to increase the available cross sectional area, and therefore reduce the pressure generated at high flow rate, is to combine the plurality of lumens within a multi-lumen catheter to support a single injection.

In one example, the power injection catheter comprises a dual lumen catheter with two corresponding input lines. At the distal end of one of the input lines a bifurcating connector (e.g., "Y" connector) is provided such that both lumens may be utilized for simultaneous injection of contrast agent at a high flow rate. When the procedure only requires low flow injection, one end of the bifurcating arms may be capped so that the two lumens may be utilized independent of each other. Optionally, a pressure buffering component/device may also be integrated into this power injecting dual lumen catheter. The pressure buffering component may be provided on one of the two input lines. For example, a pressure relief valve (PRV), a diaphragm, a burst disk, or a balloon may be integrated into the bifurcating connector.

In another variation, a multi-lumen catheter with branching extensions is configured with a valve such that the user can electively establish fluid communication between the various lumens within the catheter. In one particular design, a bifurcating dual lumen catheter is configured with a valve at the bifurcation such that the user may open the valve to establish fluid communication between the two lumens in the catheter. The user can also close the valve in the bifurcation in order to utilize the two lumens independently. In another variation, a unidirectional or a bi-directional pressure driven valve may be utilized between the two lumens. The valve may be configured to open when a predefined pressure value is exceeded. When the pressure in the first lumen exceeds the predefined pressure value, the valve opens and allows fluid to flow into the adjacent lumen to prevent overpressurizing of the first lumen.

These and other embodiments, features and advantages of the present invention will become more apparent to those skilled in the art when taken with reference to the following more detailed description of the invention in conjunction with the accompanying drawings that are first briefly described.

DETAILED DESCRIPTION OF THE INVENTION

The following detailed description should be read with reference to the drawings, in which like elements in different drawings may be identically numbered. The drawings, which are not necessarily to scale, depict selected preferred embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Before describing the present invention, it is to be understood that unless otherwise indicated this invention need not be limited to applications in humans. As one of ordinary skill in the art would appreciate, variations of the invention may be applied to other mammals as well. Moreover, it should be understood that embodiments of the present invention may be applied in combination with various catheters, drug pumps, and infusion devices.

A Peripherally Inserted Central Catheter (PICC) is used herein as an example application of the power injection catheter to illustrate the various aspects of the invention disclosed herein. One of ordinary skill in the art having the benefit of this disclosure would appreciate that the power injection catheter disclosed herein may be applicable for infusion of fluids into the circulatory system in various medical applications. It is also contemplated that the pressure relief device described herein may be implemented with various fluid infusion lines and catheters, including, but not limited to, hemodialysis catheters, central line catheters and contrast dye injection catheters.

It must also be noted that, as used in this specification and the appended claims, the singular forms "a," "an" and "the" include plural referents unless the context clearly dictates otherwise. Thus, for example, the term "a lumen" is intended to mean a single lumen or a combination of lumens, "a fluid" is intended to mean one or more fluids, or a mixture thereof.

Figure 1:
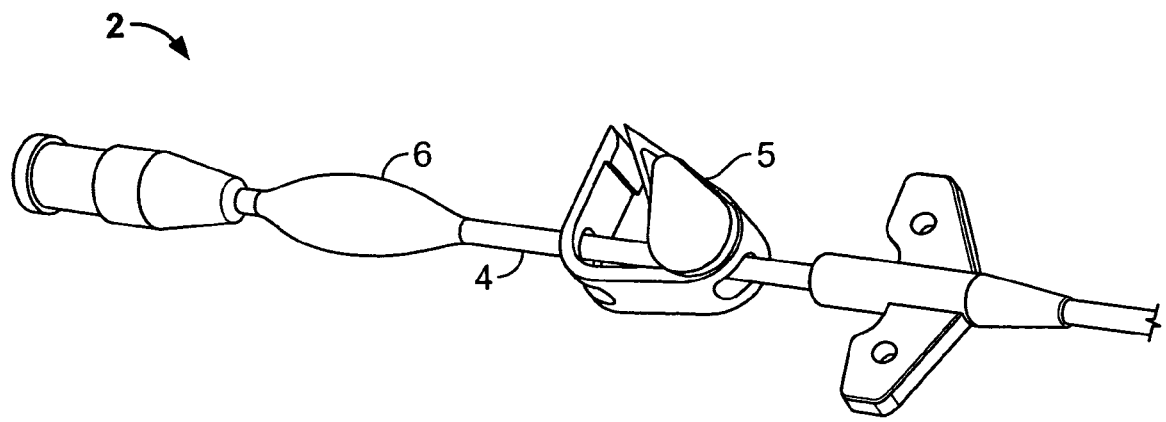
FIG. 1 illustrates one variation of a power injection catheter with a pressure relief balloon integrated into the proximal shaft of the catheter.

In one aspect of the invention, a catheter 2 comprises an elongated tubing with a pressure relief balloon 6 integrated within the body of the catheter. In one variation, the balloon 6 is integrated along the extension leg 4 of the catheter 2, as shown, for example, in FIG. 1. An optional clip 5 may be provided on the extension leg 4 to allow the user to temporarily seal the lumen of the extension leg. In another variation, the balloon may be connected to the catheter through a branch connection. The interior of the balloon is in fluid communication with the lumen of the catheter. The balloon may be comprised of a compliant, semi-compliant, or non-compliant material. In one particular variation, a non-compliant pressure relief balloon is implemented. A non-compliant balloon may provide buffering to a sudden pressure increase, but at the same time allow the operator to maintain high pressure to push the fluids through the catheter at a high rate (e.g., about 3 cc/sec or higher). For example, a typical compliant balloon may inflate at a lower pressure, such as about 100 psi, and continue to expand at pressure slightly above this value until the balloon bursts. Thus, the balloon would prevent the operator to continue to increase the pressure inside the lumen of the catheter. In a catheter with a small inner lumen, if the infusion pressure is limited, then the catheter would not be able to achieve high flow rate.

However, with a semi-compliant or non-compliant balloon, one may select materials to construct a balloon with a high burst value. For general PICC power injection applications, in one variation the balloon is configured with a burst value above about 100 psi; in another variation, the balloon is configured with a burst value above about 130 psi; in yet another variation, the balloon is configured with a burst value of at least about 200 psi. In a design with a non-compliant balloon with a high burst value, the operator is able to maintain high pressure (e.g., about 130 psi or above; in selective designs about 300 psi or above can be supported) within the lumen of the catheter to push the fluids through the catheter lumen at a high flow rate (e.g., about 4 cc/sec or above; in selective designs about 5 cc/sec or above can be supported). This design may provide the benefit of including a pressure buffering device (i.e., the pressure relief balloon) while at the same time allowing the operator to use the catheter for power injection applications (e.g., injection of contrast media at high flow rates, etc.), which require high pressures to maintain the high flow rate. As one of ordinary skill would appreciate, to achieve high flow rates one can increase the catheter lumen diameter and/or increase the pressure applied to infuse the fluid. Since the diameter of the catheter is limited by the dimension of the vessel that it's designed for, in many applications high pressures are required to maintain the high flow rate in catheters with a relatively small lumen size.

The pressure relief balloon of the present invention allows the device to buffer against sudden pressure increases, which may cause pressure spikes that exceed the catheter's burst value. The catheter body may be rated with a high burst value, but sudden pressure increases due to operator error or other factors may cause a temporary increase in pressure that exceeds the pressure threshold supported by the catheter. Without a pressure buffering medium, the catheter will likely burst. With a pressure relieving balloon, however, the pressure spike may be modulated and destruction of the catheter may be avoided.

Furthermore, one may configure the pressure relief balloon such that the balloon has a burst value that is below the burst value of the catheter. For example, the catheter body may be rated with a burst value of about 450 psi and the pressure relief balloon may be configured with a burst value of about 400 psi. In this design, when overpressure is so high (above about 400 psi), such that the balloon is unable to modulate the increased pressure, the balloon positioned at the proximal portion of the catheter will fail first and prevent damage to the catheter. Since the balloon is located at the proximal portion at the exterior of the body, it can be easily replaced or repaired without the need to surgically remove and replace the complete catheter. In another variation, one may configure the balloon such that the balloon expands minimally with moderate pressure (e.g., under about 300 psi) and expands at a much higher rate at a higher pressure (e.g., pressure above about 300 psi). In another variation, the balloon may further be configured to expand at a pressure close to the burst value of the catheter. For example, the burst value of the catheter may be about 400 psi, while the balloon expands at a higher rate at pressure above about 350 psi. In such a configuration, the expansion of the balloon indicates to the operator that the inner lumen pressure has exceeded a certain pressure threshold and the integrity of the catheter is at risk.

In the above catheter configurations, the balloon may be replaced with a diaphragm integrated within a housing including a fluid conduit. For example, a housing with a diaphragm may take the place of the balloon 6 on the device shown in FIG. 1. The fluid conduit within the housing allows the fluid to flow through, and the diaphragm serves as the pressure buffering mechanism. The diaphragm may be comprised of a compliant or semi-compliant material. In one particular variation, the diaphragm comprises a non-compliant polymeric material.

As discussed above, the balloon or diaphragm may be integrated into the external (proximal) portion of the catheter. The balloon or diaphragm serves to relieve pressure build-up and at the same time serve as a visual indicator to the operator that the catheter may be occluded and/or overpressurized. The balloon or diaphragm may also be added as an extension tube and becomes an integral part of the extension leg of the catheter. The balloon or diaphragm may be comprised of various polymeric materials or mixture thereof. For example, the balloon or diaphragm may be made of a single or double layer nylon material or of a composite material. The balloon or diaphragm may also be added to the catheter's proximal end connector and become an integral part of the connector. One of ordinary skill in the art having the benefit of the disclosure herein would appreciate that various balloon and tubing technologies that are well known in the art may also be implemented in the designs disclosed herein.

Figure 2A:
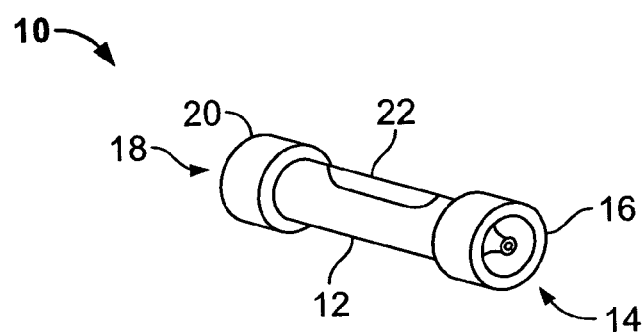
FIG. 2A illustrates a catheter inter-connector with a built-in diaphragm for modulating pressure inside the lumen of the inter-connector.
Figure 2B:
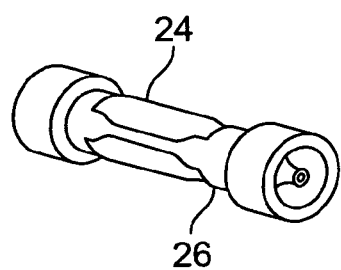
FIG. 2B illustrates a catheter inter-connector with a built-in balloon for modulating the pressure of fluid flow going through the inter-connector.

In another variation, the pressure relief device comprises an inter-connector with a built-in diaphragm. For example, the device 10 may comprise an inter-connecting tubing 12 with a male Luer Lock interface 14 at the distal end 16 of the tubing and a female Luer Lock interface 18 at the proximal end 20 of the tubing, as shown in FIG. 2A. A diaphragm 22 is provided at the mid-section of the tubing for relieving pressure build-up in the lumen of the inter-connector 12. FIG. 2B illustrates another variation of a pressure relief inter-connector where a balloon 24 is integrated into the body of the inter-connector 26. The pressure relief inter-connector may be connected to the proximal end of a catheter to provide pressure modulation to the lumen of the catheter. A fluid source may then be connected to the proximal end of the inter-connector to supply fluids into the lumen of the catheter through the inter-connector. In another variation, the pressure relieving inter-connector may be placed between two inter-connecting tubings to provide pressure modulation within the lumens of the tubing.

The diaphragm or balloon within the inter-connector may be comprised of compliant, semi-compliant, or non-compliant polymeric material. The various diaphragms and balloons described above with specific burst value or expansion characteristics may also be implemented within the inter-connector. For example, the balloon in the inter-connector may comprise a non-compliant balloon with a burst value of at least about 300 psi. In another variation, an inter-connector including a balloon or diaphragm with a lower burst value than the catheter is connected to the proximal end of the catheter to provide a fail-safe mechanism for the catheter. For example, an inter-connector with a diaphragm having a burst value of about 300 psi is connected to the proximal end of a catheter having a burst value of about 330 psi. In this variation, the inter-connector may prevent failure of the catheter due to overpressurizing since the diaphragm within the inter-connector would fail first. Since the inter-connector is removable, once it fails it can be quickly replaced and allow the medical procedure to proceed without much interruption.

Figure 2C:
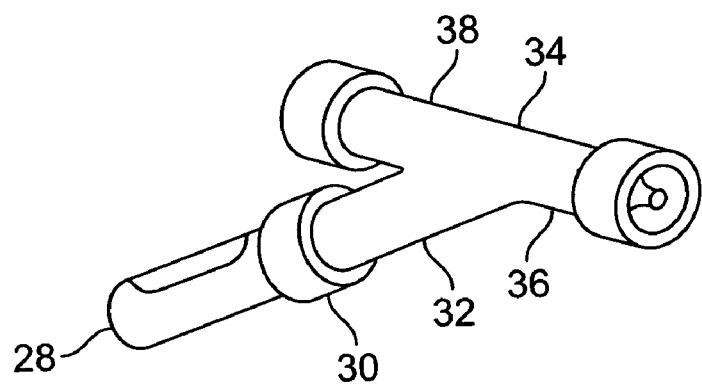
FIG. 2C illustrates another variation of a pressure relief device design where the pressure relief mechanism is provided on a side branch of a bifurcating connector.

In another variation, the inter-connectors shown in FIGS. 2A and 2B are modified with one sealed end 28 and one connection end 30. The connection end 30 of the device may be connected to a first bifurcation arm 32 of a "Y" connector 34, as shown in FIG. 2C. The primary arm 36 of the "Y" connector 34 may be connected to the proximal end of a catheter and the second bifurcating arm 38 of the "Y" connector 34 may be connected to a syringe or a fluid source. Since the pressure relieving unit is in fluid communication with the lumen of the catheter through the "Y" connector 34, the pressure relieving unit can modulate fluid pressure inside the catheter. In one variation, the pressure relieving unit may be permanently connected to the "Y" connector. In another variation, a removable pressure relieving unit is connected to the "Y" connector through an inter-connecting mechanism, such as a Luer Lock interface.

Figure 3A:
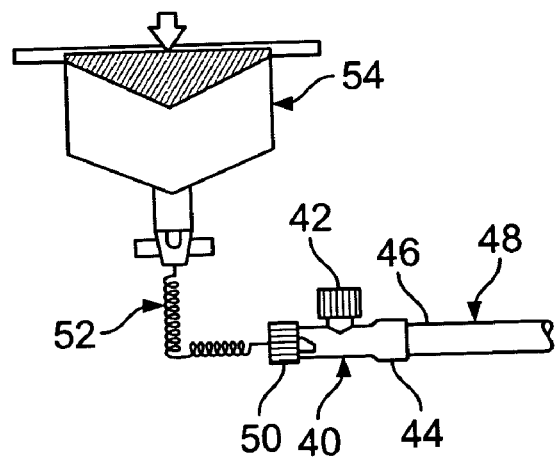
FIG. 3A illustrates a pressure relief device including one end connected to a fluid injection device and the other end connected to the proximal end of a catheter. In this variation, the pressure relief device has a pressure relief port for releasing or absorbing overpressure that occurs inside the lumen of the device.
Figure 3B:
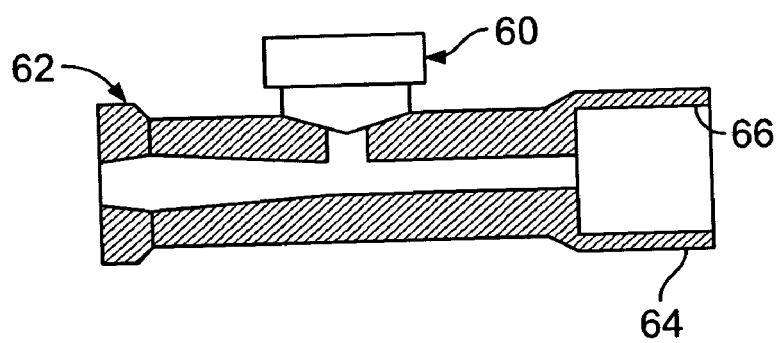
FIG. 3B shows a semi-transparent view of the pressure relief device of FIG. 3A.

In yet another variation, the inter-connecting pressure relief device comprises a side port with a pressure relieving mechanism. For example, the device may be a "T" connector with the distal port configured for connection to a catheter, the proximal port configured for connection to a syringe or fluid infusion source, and a side port configured with a pressure relief mechanism, such as a pressure relief valve, a balloon, a burst disk, or a diaphragm. In one example shown in FIG. 3A, the "T" connector 40 has a built-in pressure relief valve in the side port 42. The distal end 44 of the "T" connector 40 connects to the proximal end 46 of a power PICC catheter 48 through a Luer Lock interface. The proximal end 50 of the "T" connector 40 also has a Luer Lock connection for connecting to a tubing 52 to receive fluid from a power injection fluid source 54. In one variation, the power injection device 54 is configured with a capability of delivering a maximum pressure of about 300 psi. FIG. 3B shows a cross-sectional view of another variation of a pressure relief device. The side port 60 houses the pressure relief valve. The proximal end 62 has a female Luer Lock attachment for connection to a syringe or other tubing such as a coiled extension set. The distal end 64 has a C-Bore 66 feature to accept a power PICC tubing. In another variation, the distal end 64 may be configured with a male Luer Lock interface for connection to a catheter including a female Luer Lock interface at its proximal end.

Figure 4:
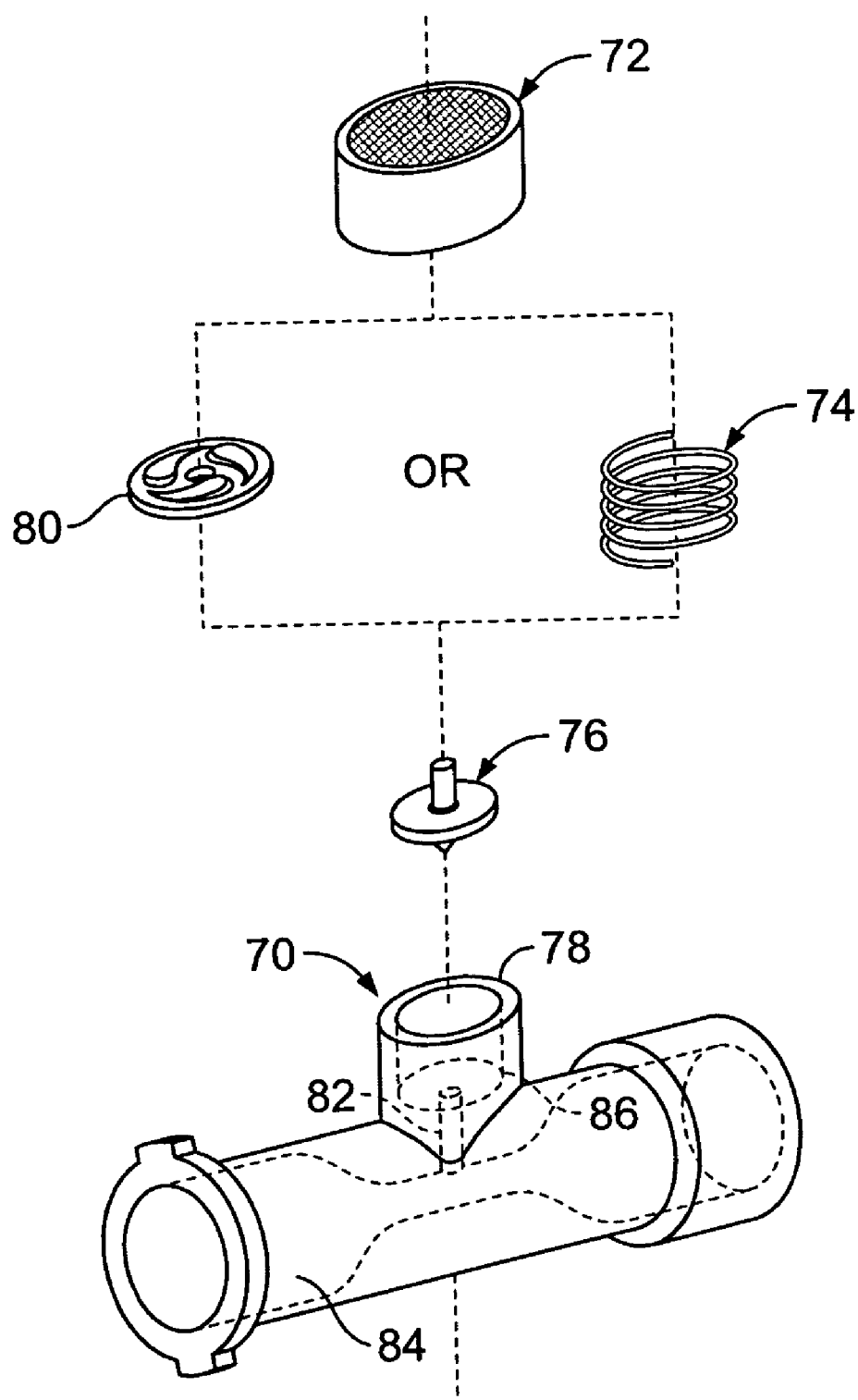
FIG. 4 illustrates one variation of a pressure relief device with a pressure relief valve incorporated in the side port of the device. The device is shown with the pressure relief valve in a disassembled state.

In one particular design, a pressure relief valve 70 comprises a spring-loaded plunger as shown in FIG. 4. A diffuser cap 72 and/or Luer Lock attachment is provided to secure a spring 74, 80 and plunger elements 76 within the side port 78. The diffuser cap 72 allows the effluent from overpressure to escape. The diffuser cap 72 may be mechanically jointed to the side port 78. A coil 74 or etched flat spring 80 is provided to maintain pressure on the plunger 76. A channel 82 within the device provides fluid communication between the lumen 84 of the inter-connector and the side port 78. Within the base of the side port, a valve seat 86 is provided to receive the plunger 76. The size of the valve seat 86 establishes the area of the valve mechanism exposed to pressure. The plunger 76 creates a seal when closed by the spring force. When the fluid flowing through the inner channel 82 into the valve seat 86 in the side port 78 builds up a pressure exceeding the force from the spring, the plunger is displaced.

The pressure from the power injection device transfers through the fluid channel and acts on the exposed area of the pressure relief valve. The exposed area multiplied by the effective pressure yields a resultant force. The resultant force of the fluid acting on the plunger/seal in the pressure relief valve is opposed by the loaded spring, which keeps the valve in the normally closed position. The magnitude of the spring force '$F_s$' is a function of the spring constant 'k' and the displacement distance 'x' (i.e., $F_s=k*x$). The magnitude of the resultant force from the fluid '$F_f$' applied on the plunger from the fluid pressure is proportional to the fluid pressure 'P' and the exposed area 'A' of the plunger (i.e., $F_f=P*A$). The interaction between the two forces, '$F_s$,' and '$F_f$,' determines the displacement of the plunger and the release of fluid from the pressure relief valve. Thus, by varying the size of the valve seat, the size of the plunger/valve, and the tension of the spring, one can configure the pressure relief valve to release pressure at a specific pressure threshold level.

Figure 5A:
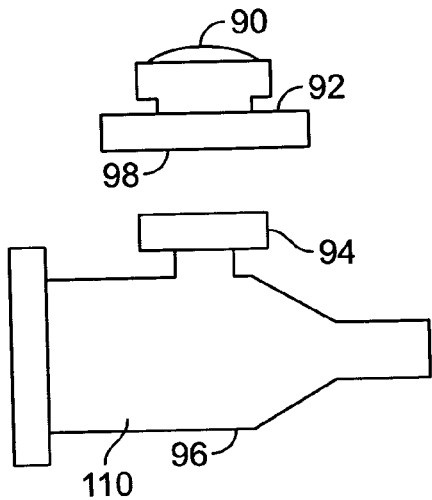
FIG. 5A illustrates another variation of a pressure relief device with a replaceable pressure relief valve for covering the side port.

In another variation of a pressure relief inter-connector, the device is configured with a replaceable pressure relief mechanism (e.g., pressure relief valve, diaphragm, balloon, etc.). The pressure relief mechanism 90 may be integrated into a cap 92 that can be mechanically connected to a side port 94 of an inter-connector 96, as shown in FIG. 5A. For example, the base 98 of the cap may have female thread matching the male thread on the side port 94 of the inter-connector, such that the cap can be easily attached to, or removed from, the inter-connector 96. Since the cap 92 is removable and replaceable, once the pressure relief mechanism 90 fails, the operator may replace it with another cap that is functional. In another variation, during the medical procedure the operator may wish to replace an existing cap with a different one that has a higher or lower pressure rating or performance characteristic in comparison with the existing one.

In one variation, the cap has an integrated balloon for pressure buffering. The balloon may be comprised of a compliant, semi-compliant or non-compliant material. For some applications, it may be desirable to implement a balloon comprising a non-compliant material. One may also select a balloon of specific burst value for implementation on the cap. For example, for power injection application where high flow (e.g., capable of delivering about 4 cc/sec or more) is required, it may be desirable to select a cap with a balloon that has a burst value of at least about 300 psi. In another variation, one may implement a cap with a burst value that is below the burst value of the catheter body, such that the balloon in the cap bursts before the catheter is overpressurized. This allows the operator to prevent accidental overpressurizing of the catheter. In the event that the balloon in the cap bursts, the operator can replace the damaged cap and proceed with the medical procedure. In another variation, a diaphragm is implemented in the replaceable cap in place of the balloon. Various material selection considerations (e.g., compliance, burst value, expansion value, etc.) that are implemented for balloon selection are also applicable for the selection of the polymeric materials for the implementation of the diaphragm.

In another design variation, a burst disk is provided between a pressure relief device and the lumen of the catheter, such that the pressure relief device is only activated when the pressure inside the lumen of the catheter exceeds the threshold of the burst disk and compromises the integrity of the burst disk (e.g., causing the burst disk to rupture), allowing the fluid inside the catheter to flow toward the pressure relief device. For example, one may select a burst disk with a burst value that is below the burst value of the catheter body, such that the burst disk will rupture and activate the pressure relief device (e.g., balloon, diaphragm, pressure relief valve, etc.) before the catheter is overpressurized.

Figure 5B:
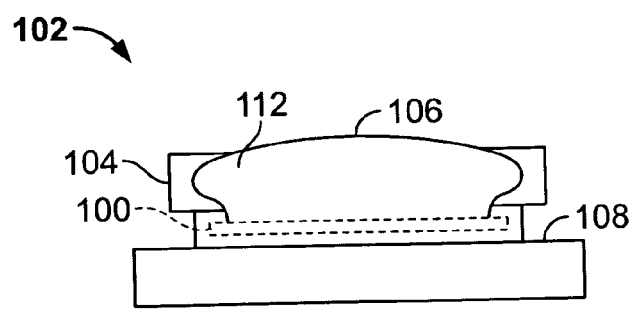
FIG. 5B shows one variation of a replaceable cap for the pressure relief valve of FIG. 5A. In this variation, the replaceable pressure relief valve has a built-in balloon and a burst disk for relieving overpressure.

In one variation, the burst disk 100 is integrated within a replaceable cap 102 as shown in FIG. 5B. The cap with the burst disk 100 may be utilized on an inter-connector 96 shown in FIG. 5A. Referring to FIG. 5B, the cap 102 comprises a housing 104 for securing a containment balloon 106 and allows for deployment of the balloon. The containment balloon 106 may comprise an elastomeric or non-elastic folded/wrapped material similar to the configuration of an airbag or angioplasty balloon. In one variation, the balloon 106 is configured with a capacity of at least about 3 cc. The containment balloon 106 may also comprise a non-compliant material. A burst disk 100 is provided on the base 108 of the housing. When the cap 102 is secured onto the inter-connector 96, the burst disk 100 provides the interface between the lumen 110 of the inter-connector 96 and the cavity 112 between the balloon 106 and the burst disk 100. The pressure threshold or burst value of the burst disk 100 may be varied by changing the materials and thickness of the burst disk. Higher strength materials and thickness may be used to achieve pressure compatible with power injection. In a particular design, the burst disk is configured to rupture before the catheter body is overpressurized and is caused to fail. For example, the burst disk may be comprised of the same polymeric material as the catheter with some modification to the material to weaken its strength or to decrease its thickness, such that the maximum pressure the burst disk can sustain is less than the maximum sustainable pressure of the catheter wall.

In one particular design, the catheter comprises a 3-French silicone catheter of 65A durometer (about 0.007 to about 0.009 inch wall thickness). Burst disks of various configurations may be applicable for integration with the 3-French catheter to prevent overpressurization. In one variation, the burst disk comprises silicone of approximately 50 A durometer. In another variation, the burst disk comprises the same silicone material used to fabricate the catheter, but the disk is configured with a thickness of less than about 0.007inches. In yet another variation, the burst disk is implemented on the catheter itself by localized weakening of catheter body using a scribe line, etching, localized thinning, etc., such that the weakened region will burst before the catheter is overpressurized. Furthermore, grooves or indentations may be etched into the catheter body as part of the localized weakening process. In one design variation, the weakened region is located at the proximal portion of the catheter.

In another design variation, a 6-French polyurethane catheter of about 78 A durometer (about 0.013 to about 0.017 inch wall thickness) is implemented with a burst disk. In one variation, polyurethane of approximately 70 A durometer is used to configure the burst disk. In another variation, the burst disk comprises silicone of approximately 70 to 80 A durometer (silicone typically has a lower burst and tear strength than polyurethane). In another variation, the burst disk comprises a sheet of material having a thickness of less than about 0.013 inches. In yet another variation, localized weakening of the catheter wall is used to implement a burst disk on a selective location directly on the catheter wall. As one of ordinary skill in the art having benefit of the disclosure herein will appreciate, the above variations may also be implemented on a multi-lumen catheter to provide a burst disk or other pressure relief mechanism for the catheter. In one variation, all the lumens in the multi-lumen catheter share the same burst disk as the pressure relief mechanism. In another variation, each lumen within the catheter is equipped with its own burst disk or pressure relief mechanism.

In another design variation, a diaphragm is used in place of the containment balloon. For example, the housing in the cap may secure a diaphragm comprised of a compliant material while a burst disk is provided at the base of the housing, such that the diaphragm only expands if the pressure inside the lumen of the catheter overcomes the burst disk and forces the burst disk to rupture. In another variation, the burst disk may be implemented with a pressure relief valve. In yet another design variation, the burst disk is implemented as the sole pressure relief mechanism without the additional balloon, diaphragm or pressure relief valve. In such a design, the fluid inside the catheter may exit the delivery system through the burst disk once the burst disk is compromised (e.g., ruptures).

As one of ordinary skill in the art having the benefit of the disclosure herein would appreciate, the implementation of the burst disk is not limited to the removable cap configuration. The burst disk may be integrated in various inter-connectors or directly on the body of the catheter, either along with other pressure relief mechanisms (e.g., balloon, diaphragm, pressure relief valve, etc.), or independently without the other pressure relief mechanisms. Furthermore, the burst disk may comprise various configurations, including, but not limited to, a disk shape. The burst disk may be comprised of compliant, semi-compliant, or non-compliant materials. The burst disk may also be configured as a membrane, or other layer of materials integrated directly into the catheter or through an attachment interface. In one design variation, the burst disk is configured such that it will be compromised (burst) and allow fluids to pass through once the pressure being exerted on it exceeds a predefined threshold.

In another aspect of the invention, an inline valve is integrated within a catheter or along the fluid path supplying fluids into the lumen of a catheter. The valve is configured such that when the pressure across the inline valve exceeds a predefined threshold, the inline valve is sealed and blocks further infusion of fluid through the valve; thus preventing the catheter, which is downstream from the valve, from overpressurizing. The inline valve may be integrated directly into the catheter or may be integrated within an inter-connector and then connected to the proximal end of a catheter. In one variation, the inline valve is positioned at the proximal portion of the catheter such that when the catheter is inserted inside the patient, the inline valve is outside the body. In this configuration, overpressurizing may be isolated to the portion of the catheter outside of the body and the portion of the catheter inside of the body is protected from overpressurizing. Furthermore, pressure relief mechanisms (e.g., balloon; diaphragm, pressure relief valve, etc.) may be provided in the fluid path upstream/proximal of the inline valve to prevent overpressurizing of the fluid supply line, which provides fluids to the catheter through the inline valve.

Figure 6A:
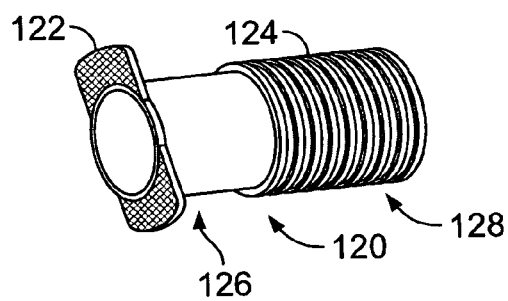
FIG. 6A illustrates another design variation comprised of an inline valve. The inline valve prevents overpressuring of the catheter lumen by blocking further fluid input when there is a sudden surge in pressure inside the catheter.

The inline valve for a catheter may be configured for attachment to the proximal end of a catheter or for insertion in between fluid supply lines. In one variation, the inline valve is integrated within an inter-connector 120 as shown in FIG. 6A. The proximal end 122 is configured for connection to a fluid supply source and the distal end 124 is configured for connection to a catheter, which is configured for insertion into a patient's body. Both the proximal 122 and the distal end 124 of the inline valve may be configured with tubing interface or connector (e.g., male/female Luer Lock or Luer Slip connections, etc.) for removable connection to catheters and/or other tubings. In the particular variation shown in FIG. 6A, the upper housing 126 is configured with a female Luer Lock interface for connection to tubings, coiled extension sets, syringes, or other fluid sources that have a male Luer Lock interface. The lower housing 128 is configured with a C-Bore in the inner lumen for solvent bond to a catheter. Alternatively, the lower housing 128 may also be configured with a removable connection interface such as a Luer Lock or Luer Slip. For example, the distal end of the lower housing may be configured with a male Luer Lock interface for receiving a female Luer Lock interface on the proximal end of a catheter. In another variation, both the proximal end and the distal end of the device are each permanently connected to a tubing.

Figure 6B:
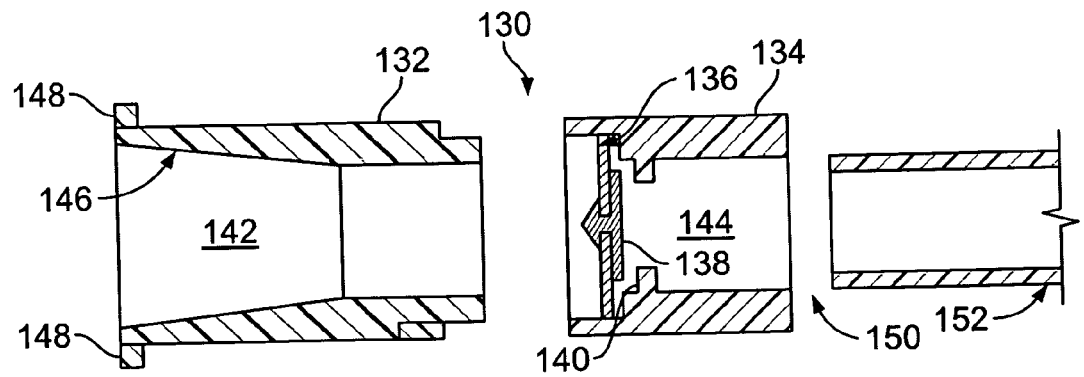
FIG. 6B shows a cross-sectional view of the pressure check valve of FIG. 6A.

Referring to FIG. 6B, the internal function of one variation of an inline valve 130 is illustrated in a cross-sectional view. The inline valve is housed within an inter-connector and comprises two connecting pieces 132, 134. An etched flat spring 136 is captured between the upper 132 and the lower 134 housing when the two housing pieces are connected to each other. The two-piece housing may be configured with solvent bond surfaces to achieve a sealed connection. In another variation, a locking interface such as matching threads may be provided on the corresponding part to secure the two housing pieces together. An elastomer seal 138 is suspended over the valve seat 140 by a flat spring 136, with fluids flowing through the flat spring 136 and around the elastomer seal 138. When the pressure difference between the inner lumen 142 of the upper housing and the inner lumen 144 of the lower housing is low, the spring 136 keeps the elastomer seal 138 away from the valve seat 140 and the fluid is allowed to flow through. When this pressure gradient overcomes the spring force, the elastomer seal 138 is forced down onto the valve seat 140 thereby arresting fluid flow through the inline valve. Once the pressure in the upper housing lumen 142 is decreased, such that the pressure across the valve is below the predefined threshold, the valve is opened to again permit fluid flow therethrough. Although in this variation an etched flat spring 136 is used to suspend the seal 138 and counteract the pressure from fluid flow, other spring materials or elastic materials may also be used in place of the etched flat spring. Furthermore, in this particular variation shown in FIG. 6B, the upper housing 132 is configured with a female Luer taper 146 in the proximal portion of the inner lumen 142 for receiving a male Luer. Luer ears 148 are provided at the proximal edge of the housing for mating with threads in a male Luer Lock interface. The distal portion 150 of the lower housing 134 is configured for receiving a catheter 152. The catheter 152 may be solvent bond to the lower housing 134.

In another variation, the inline valve is configured, such that the valve closes before the pressure inside the lumen of the catheter connected to the distal end of the inline valve exceeds its bursting pressure. For example, one may select a spring with a higher spring coefficient for a catheter having a high burst value, while using a spring with a lower spring coefficient for applications where a catheter with a lower burst value is being implemented. In another application, inter-connectors with embedded inline valves of varying sealing/closing pressure threshold may be provided, such that the operator may select the desired overpressure protection by connecting the appropriate inline valve to the proximal end of the catheter. For example, the catheter may have a burst pressure of about 400 psi, thus, one may design the inline valve to close before the pressure across the valve reaches about 300 psi to prevent the catheter from being overpressurized.

In another aspect of the invention, a multi-lumen catheter is configured for high flow infusion applications. A catheter having a plurality of lumens is designed, such that different fluids may be injected through the various lumens independently, or the operator may reconfigure the catheter, such that all the lumens are used simultaneously to deliver fluid from a single source at a high flow rate. For example, an elongated catheter body having a plurality of lumens running in parallel from the proximal end of the catheter to the distal end of the catheter may be prepared with a plurality of extension tubings connected to the proximal end of the catheter body for providing independent fluid paths to each of the lumens within the catheter body. A fluid inter-connector with multiple branching is attached to the proximal end of the first extension tubing. The fluid inter-connector has an input port and a plurality of output ports for connection to the proximal end of the plurality of extension tubings. The connection to the first tubing may be a permanent connection or it may be achieved through a Luer Lock type interlocking connection. Sealing caps may be implemented to close the unused output ports when the input port on the inter-connector is used for fluid delivery into the first tubing only. When the catheter is to be used for simultaneous injections of a single fluid through all the lumens, the sealing cap may be removed and the corresponding extension tubings may be attached to the inter-connector to receive fluid from the input valve of the inter-connector. A fluid source may then be connected to the input port of the inter-connector and fluids injected into the input port are diverted down the various extension tubings and then into the various lumens within the catheter body.

The output ports of the inter-connector and the proximal end of the tubings may be configured with matching interlocking interface for removable connections. For example, each of the output ports of the inter-connector may be configured with a male Luer Lock interface, while the proximal end of each of the extension tubings may be configured with a female Luer Lock interface. Furthermore, the multi-output inter-connector may be provided with a switch, such that the operator may select "one input one output" mode or "one input multiple outputs" mode. With the selection switch, one would not need the sealing caps to terminate the open output ports when the lumens of the catheter are being used independent of each other for fluid delivery.

Figure 7A:
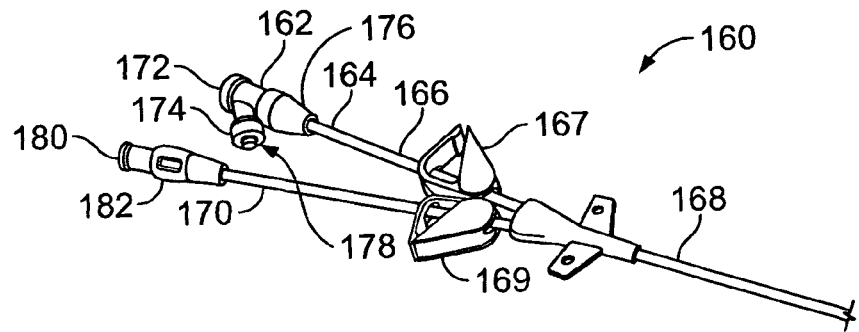
FIG. 7A illustrates another variation of a power injection catheter. The catheter comprises a dual lumen design with the capability for simultaneous high flow injection through the implementation of a bifurcating connector.

FIG. 7A shows one particular variation of a dual lumen (D-shaped) catheter 160 that supports both simultaneous injections through both lumens (e.g., injection of contrast media through both lumens, etc.) for high flow applications, which may be reconfigured for low flow applications where each of the lumens can be used independent of each other for various infusion therapy or blood withdrawal. An inter-connector 162 is constructed to allow independent use of both lumens/extensions where only low flow rate (e.g., about 5 cc/sec or less) is required. As shown in FIG. 7A, a "Y" connector 162 is provided at the proximal end 164 of a first extension leg 166. The lumen of the first extension leg 166 is in fluid communication with one of the two lumens within a main catheter body 168. A second extension leg 170 is provided for delivering fluids into the second lumen within the main catheter body 168. The "Y" connector 162 has an input port 172 and two output ports 174, 176, and the first output port 176 is connected to the first extension leg 166. The second output port 174 is provided with a male Luer Lock interface 178, and the proximal end 180 of the second extension leg 170 is provided with a matching female Luer Lock interface 182. For low flow applications, the second output port 174 may be closed by a cap. Two separate fluid sources may be provided to direct fluids into the two extension legs 166, 170. One may also use one extension leg for blood withdrawal and the other for infusion of medication. A clip 167, 169 may be provided on each of the extension legs 166, 170 to allow the user to selectively close the fluid channel supported by any one of the two extension legs.

Figure 7B:
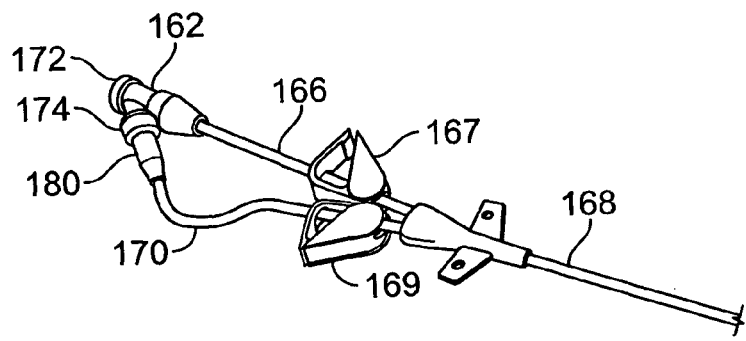
FIG. 7B shows the power injection catheter of FIG. 7A configured for simultaneous high flow injection. The secondary branch is connected to the primary branch through the bifurcating connector.

For high flow applications, one may remove a cap placed on the second output port 174 of the "Y" connector 162, and connect the proximal end 180 of the second extension leg 170 to the second output port 174, as shown in FIG. 7B. In this configuration, fluid injected through the input port 172 of the "Y" connector 162 will flow into both of the extension legs 166, 170 and be directed into both of the lumens within the main catheter body 168, thus allowing simultaneous injection of fluid through both of the lumens. One may also use this configuration to withdraw blood or other fluids from a patient's body through both of the lumens simultaneously. The inter-connector 162 may further be designed to provide equal flow into both of the lumens, such that injection of the fluids through the inter-connector would result in even distribution of pressures into both of the lumens. Once the high flow injection application is accomplished, one may remove/disconnect the second extension leg from the inter-connector and terminate the second output port so that each of the lumens may again be used independently for fluid infusion or extraction.

Figure 8A:
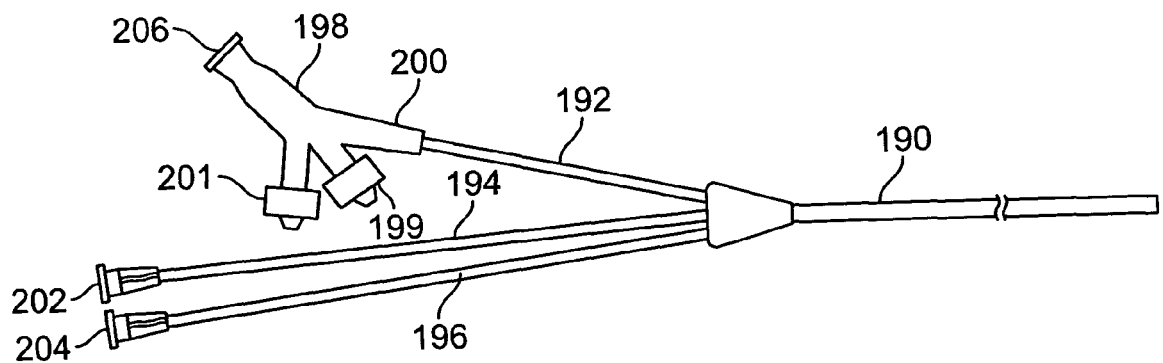
FIG. 8A illustrates yet another variation of a power injection catheter having three lumens. A fluid inter-connector having three output branches is implemented in this variation for simultaneous delivery of fluids into the three separate lumens.

One of ordinary skill in the art having the benefit of the disclosure herein would appreciate that variations of the multi-output inter-connector may be implemented on catheters having three or more lumens to provide the capability for simultaneous injections of a fluid through all the lumens. FIG. 8A illustrates one example where the main catheter body 190 has three lumens, and three extension leg tubings 192, 194, 196 are provided for supplying fluids to each of the lumens. A four-port inter-connector 198 is provided, such that the catheter can be configured for simultaneous injections through all three lumens. In this particular variation, a first port 200 on the inter-connector is connected to the first leg extension 192. Second 199 and third ports 201 are available for connection to the proximal end 202, 204 of the other two leg extension 194, 196. A fourth port 206 is provided for connection to a fluid source. Furthermore, it is contemplated that in another design, the multi-lumen catheter may be configured, such that not all the lumens are implemented for simultaneous injections. For example, in a triple lumen catheter, the inter-connector may only support two extension legs, such that only two of the three lumens are used for simultaneous injections, and the third lumen may be utilized independent of the other two lumens which are linked through the inter-connector.

Figure 8B:
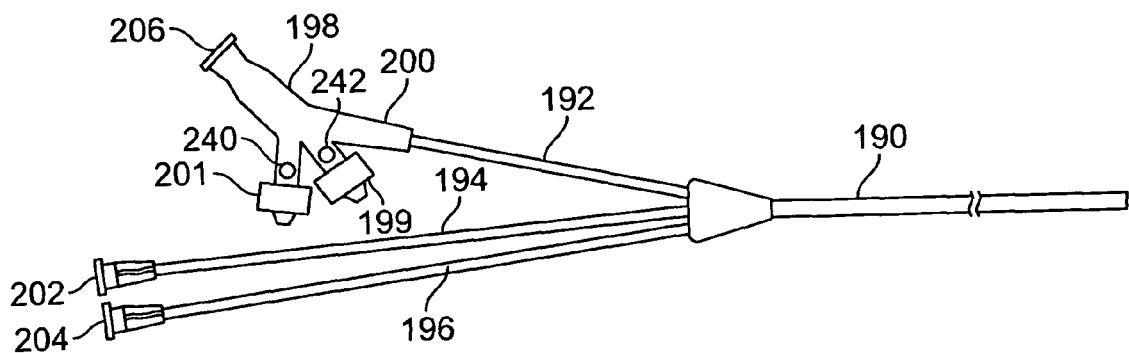
FIG. 8B illustrates another variation of a power injection catheter with gates integrated within the inter-connector to allow the user to open and close selective ports.

In another variation, the "Y" connector 162 further comprises a switch or gate that allows the user to close the additional output port when it is not in use. For example, as shown in FIG. 8B, gates 240 and 242 are provided on the two output ports, 201 and 199 respectively. When the two output ports 102, 199 are not in use, the use may close them so that the leg extension 192 connected to the inter-connector 198 may be used independently for fluid infusion or aspiration.

Figure 9:
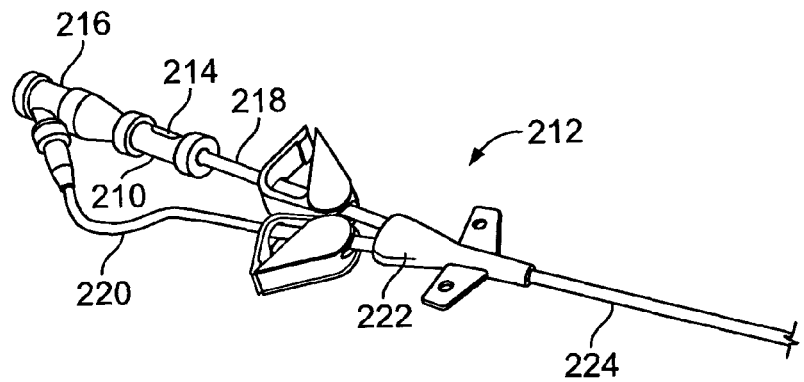
FIG. 9 illustrates another variation of a power injection catheter with a built-in pressure relief mechanism. In this variation, the pressure relief mechanism is integrated into one of the extension arms.

In another variation, a pressure relief mechanism (e.g., balloon, diaphragm, burst disk, pressure relief valve, etc.) 210 may be implemented on the multi-lumen catheter with simultaneous injection capability 212. For example, as shown in FIG. 9, a balloon 214 may be integrated into the inter-connector (i.e., "Y" connector) 216 of a dual lumen catheter. In another variation, a pressure relief valve may be design into the inter-connector 216. It is also contemplated that the pressure relief mechanism may be built into either of the extension legs 218, 220. One may also place the pressure relief mechanism in the bifurcation 222, which provides the branching to the two extension legs 218, 220. In addition, pressure relieving mechanism may also be integrated directly into the main catheter body 224.

Figure 10:
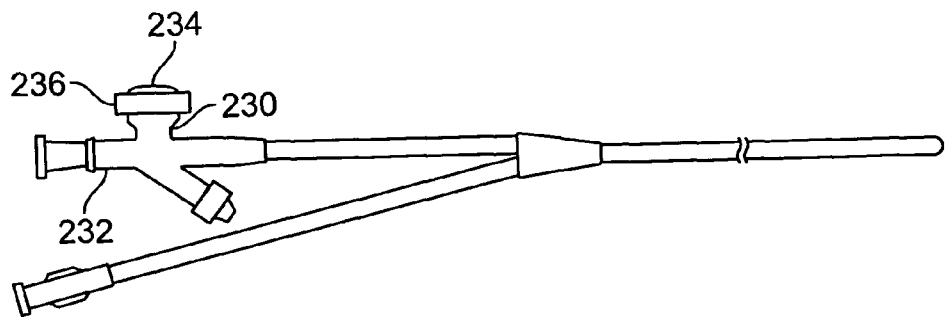
FIG. 10 illustrates another variation of a power injection catheter with a pressure relief mechanism implemented on a side branch of the fluid inter-connector.

FIG. 10 illustrates one variation where an additional branch 230 is provided on the inter-connector 232 for supporting a pressure relief mechanism 234. In this particular variation, the branching 230 is configured to receive a housing 236 with an embedded balloon 234. The housing 236 may be configured as a removable cap so that the balloon can be easily replaced. A burst disk may also be integrated within the housing 236 such that the pressure relief mechanism (i.e., the balloon) only activates when the pressure inside the inter-connector 232 exceeds the pressure threshold and compromises the burst disk. In another variation, the housing 236 may simply comprise a burst disk without an additional pressure relief mechanism. One of ordinary skill in the art having the benefit of this disclosure would appreciate that the inter-connector may be configured with both the fluid port control gate and the pressure relief mechanism.

In yet another variation, an additional inter-connector with built-in pressure relief mechanism, such as the ones shown in FIG. 2A, 2B, 3B, 5A, 6A, may be attached to either the input port or one of the output ports of the "Y" connector to provide the pressure relieving capability to the multi-lumen catheter, such as the one shown in FIG. 7A. For example, the dual lumen catheter of FIG. 7A may be provided with pressure relieving capability by adding an inter-connector, with a built-in pressure relief mechanism, to the input port of the "Y" connector. In another design, the device shown in FIG. 9 may comprise three detachable parts: (1) a dual lumen catheter with two leg extensions, (2) a "Y" connector inter-connector, and (3) an inter-connector with a built-in pressure relief mechanism. Each of the three parts is configured with a connection interface for forming the desired device. Because each of the three parts is removable from the device, if one of the parts malfunctions, the operator may replace the specific malfunctioning part without replacing the whole device.

The multi-lumen catheter with simultaneous-injection capability may be inserted into patients through various catheter placement procedures that are well known to one of ordinary skill in the art. For example, the multi-lumen catheter may be inserted through a vein in the patient's arm. Once the catheter is inserted, the distal portion of the catheter may be threaded up the vessel toward the heart. In one variation, the distal tip of the catheter is placed within the patient's superior vena cava. Once the catheter is secured in place, the physician may then utilize the individual fluid paths provided by the multi-lumen for injection of fluids, medication, or nutrients. The physician may also use one or more of the lumens to withdraw blood from the patient's circulatory system. For high flow rate power injection applications, the physician may configure the power injection catheter by connecting all the extension legs to the inter-connector and simultaneously inject fluids into all the lumens in the catheter from a single fluid source. Once the power injection is completed, the physician may reconfigure the extension legs for individual infusion.

Figure 11A:
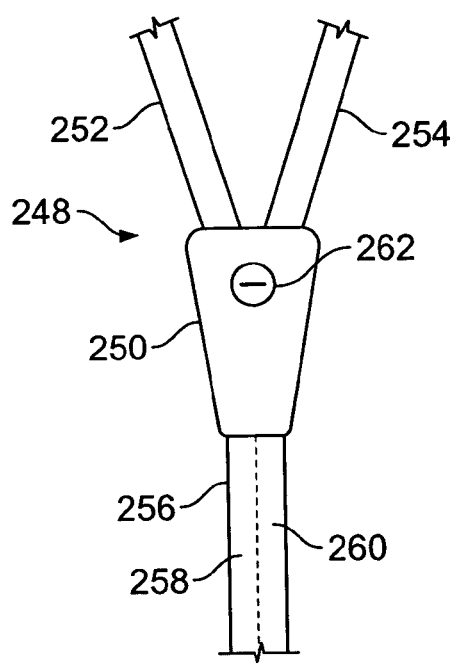
FIG. 11A illustrates one variation of a bifurcating catheter with an integrated valve within the bifurcation to control fluid flow between the two fluid channels within the catheter. The valve is shown in the open position to allow fluid communication between the two channels.
Figure 11B:
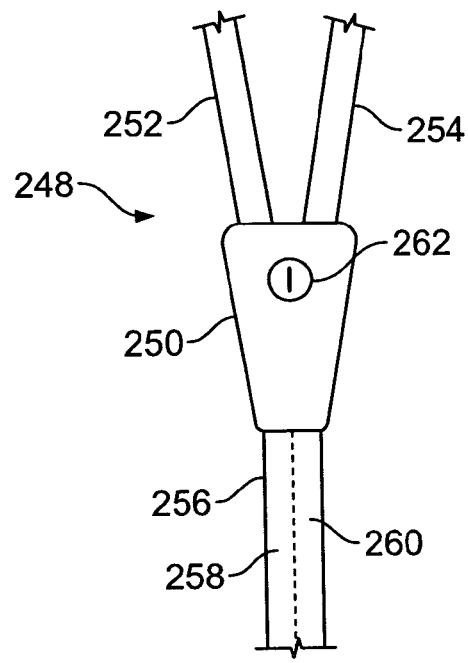
FIG. 11B illustrates the bifurcating catheter of FIG. 11A with the valve in the closed position preventing fluid flow between the two fluid channels.

In another variation, a multi-lumen catheter is configured with one or more valves such that fluid communication is established between the various lumens within the catheter. Referring to FIG. 11A, one variation of a dual lumen catheter 248 with bifurcating arms 252, 254 is configured with a valve 262 on the bifurcation 250. The valve may be a stop-cock like device molded into the catheter bifurcate. When the valve is turned horizontally, as shown in FIG. 11A, fluids can flow between the first lumen 258 and the second lumen 260. When the valve is turned vertically, as shown in FIG. 11B, the two lumens are separated, and each of the lumens can be utilized for independent fluid delivery. As one of ordinary skill in the art would appreciate, various other valves may also be implemented to provide user control of fluid flow between the two adjacent lumens within the catheter.

Figure 12:
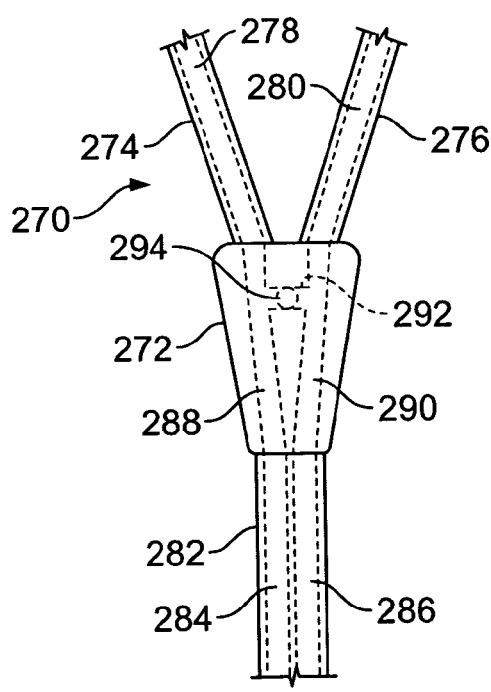
FIG. 12 illustrates another variation of a bifurcating catheter with a pressure driven valve positioned within the bifurcation to permit fluid communication between the two fluid channels supported by the catheter.

In another variation, a pressure driven valve may be implemented between the plurality of lumens within a multi-lumen catheter. For example, as shown in FIG. 12, a valve 294 that opens at a pre-designated pressure (i.e., a pop-valve, etc.) can be implemented within the bifurcation 272 to allow fluid flow between the two lumens 288, 290 within the dual lumen catheter 270. The valve maintains the closed position when pressure gradient between the two lumens 288, 290 is below a predetermined level. The valve opens when the pressure gradient exceeds a pre-designated pressure and allows the fluid to flow from one lumen to the other. In one application, the user injects fluids through the first extension leg 274 and fluids flow from the first lumen 278 through the corresponding lumen 288 within the bifurcation into the first lumen 284 within the dual lumen catheter 282 when the injection pressure is below the pre-designated pressure. When the pressure within the first lumen 288 exceeds the pre-designated pressure, the valve 294 opens and allows fluid to flow into the second lumen 290 in the bifurcation. The proximal end of the second extension leg may be closed such that fluid entering the second lumen 290 may be directed into the second lumen 286 within the dual lumen catheter 282.

In one variation, the valve is configured to open when the pressure gradient across the valve is above the pressure required for typical medication infusion (e.g., below 60 psi.). Either a unidirectional valve or a bidirectional valve may be utilized depending on the particular application. In one configuration, a bidirectional valve is used, such that excessive pressure can be shunted to the adjacent lumen in either direction. The bidirectional valve may also normalize the pressure between two lumens when both of the extension legs 274, 276 are utilized simultaneously for fluid injection. When the pressure within either one of the lumen 278 or 280 is greater then the pressure within the adjacent lumen by a pre-determined amount, the bidirectional valve would open and allow the pressure between the two lumens 278, 280 to normalize. In another variation, two valves are placed between the two lumens 288, 290, such that one valve would open when the first lumen 288 is overpressurized, while the other valve would open when the second lumen 290 is overpressurized.

In yet another variation, the valve mechanism is integrated within an adaptor coupled to a multi-lumen catheter to permit fluid communication between the lumens of the catheter. The valve mechanism may comprise a manual valve that allows the user to control the fluid flow between the lumens. In another variation, the valve mechanism comprises a pressure valve. For example, the valve may be configured with a pre-defined threshold value, such that when the pressure within one lumen of the catheter exceeds the pressure within an adjacent lumen of the catheter by the predefined amount, the valve opens up and relieves pressure within the lumen with the higher pressure. The valve in the adapter may be a bidirectional valve or a unidirectional valve.

Figure 13:
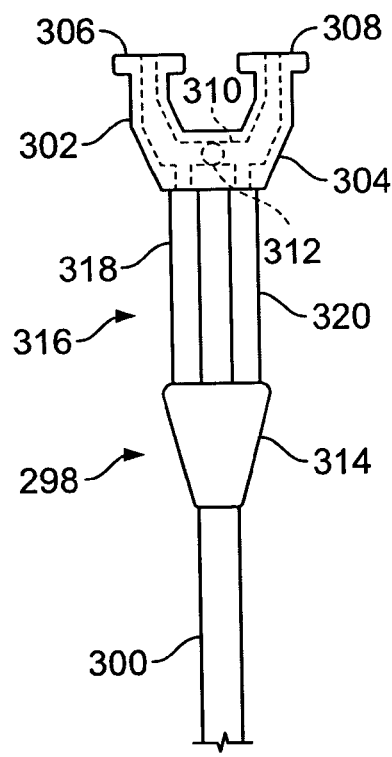
FIG. 13 illustrates another variation where an adaptor including a valve is attached to a bifurcating catheter to provide fluid communication between the to fluid channels supported within the bifurcating catheter.

In one example, a luer connection 302 on a bifurcating catheter 298 is provided with a valve mechanism 312, as shown in FIG. 13. The bifurcating catheter 298 comprises a dual lumen catheter 300 with a bifurcation 314 supporting two bifurcating branches 318, 320, each of which connects to the luer connection 302. The luer connection 302 comprises two locking interfaces 306, 308 which may be utilized for connection to a fluid source, a suction source, or other catheters. A valve 312 is provided in the channel 310 connecting the two lumens within the luer connection 302.

In another example, the bifurcating branches 318, 320 are provided with luer interfaces on their proximal ends. An adapter, similar to the luer connector 302 shown in FIG. 13, is provided for connection to the two bifurcating branches 318, 320 through the luer interfaces on the bifurcating branches. The distal end of the adaptor may be provided with matching interfaces to receive the two bifurcating branches. Once the adapter is connected to the bifurcating catheter, a structure similar to the one shown FIG. 13 is formed.

In yet another example, the proximal end of a dual lumen catheter is connected directly onto a luer connector similar to the one 302 shown in FIG. 13. Additional tubings may be connected to the luer interfaces 306, 308 to infuse fluid into the dual lumen catheter. The built-in valve in the luer connection modulates fluid flow between the two lumens within the dual lumen catheter. One of ordinary skill in the art having the benefit of this disclosure would appreciate that luer connectors or adaptors with an integrated valve supporting interlumen fluid communication may be configured to support catheters with three or more lumens.

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed as new and desired to be protected by Letters Patent of the United States is:

1. A catheter comprising:
   an elongated catheter body including a plurality of lumens open to a circulatory system of a patient;
   a plurality of extension tubings, each tubing including a lumen in fluid communication with one of the catheter body lumens; and
   an inter-connector, which allows the maintenance of pressure of at least 300 psi, comprising:
      an input port and a plurality of output ports, the output ports in fluid communication with the input port, each of the output ports configured for connection to a proximal end of one of the extension tubings, at least one of the extension tubings connected to one of the output ports;
      a pressure relief mechanism disposed exterior to a patient body and configured to prevent overpressurizing in at least one of the lumens of the catheter body; and
      an indicator indicating when a threshold pressure inside the inter-connector has been exceeded.

2. The catheter according to claim 1, wherein the proximal ends of each of the plurality of extension tubings are configured for connection to the inter-connector such that fluid can be simultaneously injected into each of the plurality of lumens from a single fluid source.

3. The catheter according to claim 1, wherein the inter-connector further comprises a switch for limiting fluid flow to one of the output ports.

4. The catheter according to claim 1, wherein the pressure relief mechanism comprises a balloon, a diaphragm, a pressure relief valve, and/or a seal positioned over a valve opening and an etched flat spring configured to apply a force on the seal.

5. The catheter according to claim 1, further comprising an inline valve positioned along the length of one of the extension tubings.

6. The catheter according to claim 1, wherein the pressure relief mechanism includes a diaphragm, a burst disk, and/or a pressure relief valve.

7. The catheter according to claim 1, wherein the pressure relief mechanism includes a balloon.

8. The catheter according to claim 7, wherein the pressure relief mechanism includes a burst disk configured to activate the balloon when the lumen pressure within the catheter exceeds a pressure threshold and compromises the burst disk.

9. The catheter according to claim 1, wherein the elongated catheter body comprises two lumens.

10. The catheter according to claim 9, wherein the inter-connector comprises a bifurcating fluid connector including two bifurcating branches.

11. The catheter according to claim 10, wherein the bifurcating fluid connector further comprises a switch for controlling fluid outflow through one of the bifurcating branches.

12. The catheter according to claim 10, wherein the bifurcating fluid connector is configured to permit equal flow into both of the lumens in the catheter body.

13. The catheter according to claim 10, wherein the bifurcating fluid connector includes the pressure relief mechanism.

14. The catheter according to claim 10, wherein the catheter is configured to support a combined fluid flow rate of at least about 5 cc/sec through both of the lumens.

15. The catheter according to claim 10, wherein the catheter is configured to support a combined fluid flow rate of at least about 7 cc/sec through both of the lumens.

* * * * *